(12) United States Patent
Cinquin et al.

(10) Patent No.: US 9,017,884 B2
(45) Date of Patent: Apr. 28, 2015

(54) GLUCOSE BIOFUEL CELL

(75) Inventors: Philippe Cinquin, Saint Nazaire les Eymes (FR); Chantal Gondran, Grenoble (FR); Fabien Giroud, Chevrieres (FR); Serge Cosnier, Crolles (FR)

(73) Assignee: Universite Joseph Fourier, Grenoble Cedex (FR)

( * ) Notice: Subject to any disclaimer, the term of this patent is extended or adjusted under 35 U.S.C. 154(b) by 985 days.

(21) Appl. No.: 12/944,381

(22) Filed: Nov. 11, 2010

(65) Prior Publication Data

US 2011/0250510 A1 Oct. 13, 2011

(30) Foreign Application Priority Data

Apr. 8, 2010 (FR) ...................................... 10/52657

(51) Int. Cl.
*H01M 8/16* (2006.01)
*H01M 4/90* (2006.01)
*C12N 9/04* (2006.01)
*C12N 9/02* (2006.01)

(52) U.S. Cl.
CPC ............... *H01M 8/16* (2013.01); *C12N 9/0006* (2013.01); *C12N 9/001* (2013.01); *C12N 9/0055* (2013.01); *C12N 9/0071* (2013.01); *H01M 4/90* (2013.01); *Y02E 60/527* (2013.01)

(58) Field of Classification Search
None
See application file for complete search history.

(56) References Cited

U.S. PATENT DOCUMENTS

| 6,030,720 | A | * | 2/2000 | Chu et al. ....................... 429/105 |
| 2005/0106425 | A1 | * | 5/2005 | Damore et al. .................. 429/12 |
| 2010/0221644 | A1 | * | 9/2010 | Nakagawa et al. ........... 429/523 |
| 2011/0065008 | A1 | * | 3/2011 | Nakagawa et al. ........... 429/401 |

FOREIGN PATENT DOCUMENTS

| JP | 2008-060067 | * | 3/2008 |
| WO | 2009/136092 A1 | | 11/2009 |
| WO | WO 2009/136548 | * | 11/2009 |

OTHER PUBLICATIONS

Pizzariello et al., "A glucose/hydrogen peroxide biofuel cell that uses oxidase and peroxidase as catalysts by composite bulk-modified bioelectrodes based on a solid binding matrix", Bioelectrochemistry, 56 (2002) p. 99-105.*
Ivanof, Vidakovic-Koch and Sundmacher: "Recent Advances in Enzymatic Fuel Cells: Experiments and Modeling", Energies, (2010; published Apr. 21, 2010) ISSN 1995-1073, www.mdpi.com/journal/energies.
French Search Report issued in 10/52657 on Sep. 21, 2010.

(Continued)

*Primary Examiner* — Jonathan Crepeau
(74) *Attorney, Agent, or Firm* — Vedder Price P.C.

(57) ABSTRACT

A biofuel cell intended to be immersed into a liquid medium containing a sugar and oxygen, wherein the anode includes an enzyme capable of catalyzing the oxidation of the sugar and a redox mediator of low redox potential capable of exchanging electrons with the anode enzyme and the cathode includes an enzyme capable of catalyzing the reduction of oxygen and a redox mediator of high redox potential capable of exchanging electrons with the cathode enzyme. Each of the anode and cathode electrodes is formed of a solid agglomerate of a conductive material mixed with the appropriate enzyme and redox mediator and is solid with an electrode wire.

8 Claims, 1 Drawing Sheet

(56) References Cited

OTHER PUBLICATIONS

S. Cosnier et al., "An easy compartment-less biofuel cell construction based on the physical co-inclusion of enzyme and mediator redox within pressed graphite discs", Electrochemistry Communication, vol. 12, No. 2, Feb. 1, 2010, XP026858666.

"N. Kakehi and AL: A Novel wireless glucose sensor employing direct electron transfer principle based enzyme fuel cell", Biosensors and Bioelectronics, vol. 22, Jan. 1, 2007, XP002600793.

S. Cosnier and AL: "Carbon cavity microelectrode for electrical wiring of enzyme by insoluble electroactive species in aqueous media", Electroanalysis, Jan. 1, 2008, XP002600794.

Kuwahara T., et al.: "Fabrication of enzyme electrodes with a polythiophene derivative and application of them to a glucose fuel cell", Synthetic Metals, vol. 159, No. 17-18, Sep. 1, 2009, XP026564940.

Cinquin, P. and AL: "A glucose biofuel cell implanted in rats", Plosone, vol. 5, No. 5, E10476 May 1, 2010, XP002600796.

\* cited by examiner

GLUCOSE BIOFUEL CELL

BACKGROUND OF THE INVENTION

1. Field of the Invention

The present invention relates to biofuel cells of sugar-oxygen type, for example, glucose-oxygen cells, that is, fuel cells capable of converting part of the power available in a biodegradable substrate into electricity.

2. Discussion of Prior Art

Various types of glucose-oxygen biofuel cells are described in prior art, for example, in patent application PCT/FR2009/050639 (B8606). In such known biofuel cells, each electrode, anode and cathode, corresponds to an enclosure containing a liquid medium into which an electrode wire is plunged. The anode and cathode enclosures are delimited by membranes capable of being crossed by hydrogen and oxygen but preventing the circulation of other heavier elements.

The anode comprises an enzyme and a redox mediator in a solution. The enzyme is capable of catalyzing the oxidation of sugar and is for example selected from the group comprising glucose-oxidase if the sugar is glucose and lactose-oxidase if the sugar is lactose. The redox mediator has a low redox potential enabling to exchange electrons with the anode enzyme and is for example selected from the group comprising: ubiquinone (UQ) and ferrocene.

The cathode also comprises an enzyme and a redox mediator in a solution. The enzyme is capable of catalyzing the reduction of oxygen and is for example selected from the group comprising: polyphenol oxidase (PPO), laccase and bilirubin oxidase. The redox mediator has a high redox potential enabling to exchange electrons with the cathode enzyme and is for example selected from the group comprising: hydroquinone (QHD) and 2,2'-azinobis-(3-ethylbenzo-thiazolin-6-sulphonate) (ABTS).

Reactions of the following type then occur at the anode and at the cathode:

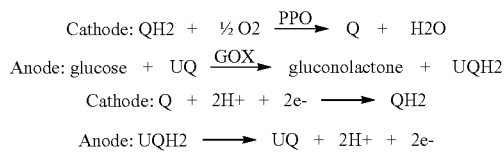

these reactions being provided in the specific case where the sugar is glucose, the anode enzyme is glucose oxidase (GOX), the anode redox mediator is ubiquinone (UQ), the cathode enzyme is polyphenol oxidase (PPO), and the cathode redox mediator is quinhydrone (QH2). A 20-mV anode potential and a 250-mV cathode potential are then obtained, which results in a 230-mV zero-current potential difference of the biofuel cell.

Such biofuel cells operate properly but, especially relating to the biofuel cell described in patent application PCT/FR2009/050639, they require for the anode and cathode conductors to be plunged into enclosures containing suitable liquids, which is a practical disadvantage in many cases and makes it in particular very difficult, or even impossible, to implant such biofuel cells in a living being.

Indeed, such biofuel cells are attempted to be implanted in living beings, especially to power various actuators, such as pacemakers, artificial sphincters, or even artificial hearts.

Biofuel cells with solid electrodes have been provided. However, biofuel cells using such electrodes, especially when they are implanted in a living being, have a very short lifetime.

SUMMARY OF THE INVENTION

Thus, according to an embodiment of the present invention, biofuel cells which are easy to handle and that can in particular be implanted in a living being, be it animal or human, are desired to be formed.

More specifically, an embodiment of the present invention provides a biofuel cell intended to be immersed in a liquid medium containing a sugar and oxygen, wherein the anode comprises an enzyme capable of catalyzing the oxidation of the sugar and a redox mediator of low redox potential capable of exchanging electrons with the anode enzyme, and the cathode comprises an enzyme capable of catalyzing the reduction of oxygen and a redox mediator of high redox potential capable of exchanging electrons with the cathode enzyme, wherein each of the anode and cathode electrodes is formed of a solid agglomerate of a conductive material mixed with the appropriate enzyme and redox mediator and is solid with an electrode wire; and the anode and cathode electrodes are surrounded with a semipermeable membrane letting through oxygen and glucose and blocking the enzyme and the redox mediator.

According to an embodiment of the present invention, the anode and cathode electrode assembly is surrounded with a semipermeable membrane letting through glucose and oxygen and impermeable to enzymes and redox mediators.

According to an embodiment of the present invention, the membranes are dialysis-type membranes.

According to an embodiment of the present invention, the cathode mediator is selected from the group comprising quinone, ABTS, osmocene, ruthenocene, cobalt (II) tetraphenylporphyrin, and zinc phthalocyanine.

According to an embodiment of the present invention, the cathode enzyme is selected from the group comprising polyphenol oxidase (PPO), laccase, and bilirubin oxidase.

According to an embodiment of the present invention, the anode mediator is selected from the group comprising ubiquinone, ferrocene, cobaltocene, methylphenothiazine, and 8-hydroxyquinoline-5-sulfonic acid hydrate (HQS).

According to an embodiment of the present invention, the anode enzyme is selected from the group comprising glucose oxidase, lactose oxidase, galactose oxidase, and fructose oxidase, according to the sugar to be converted.

According to an embodiment of the present invention, the conductive material is graphite.

According to an embodiment of the present invention, the conductive material is a conductive polymer.

Another embodiment of the present invention provides a method for manufacturing a biofuel cell, according to which the anode and the cathode are formed by compression of a dissolved mixture comprising a conductor associated with an appropriate enzyme and redox mediator.

The foregoing and other objects, features, and advantages of the present invention will be discussed in detail in the following non-limiting description of specific embodiments in connection with the accompanying drawings.

DETAILED DESCRIPTION

Figure 1:
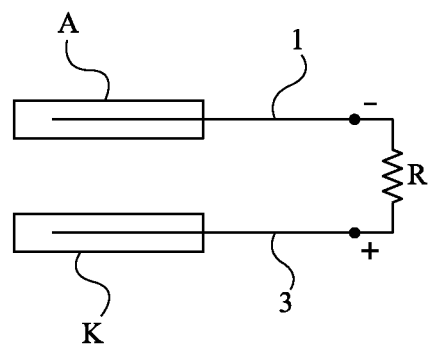
FIG. 1 very schematically shows a biofuel cell with solid electrodes.

FIG. 1 shows a biofuel cell connected to a load R. This biofuel cell comprises an anode body A and a cathode body K. The anode body is formed of a solid body comprising a conductive material associated with an appropriate anode enzyme and redox mediator. The anode body is solid with an anode wire 1. Similarly, the anode is formed of a solid body formed of a conductor associated with an appropriate enzyme and cathode mediator. The cathode body is solid with a cathode wire 3. The anode and cathode wires, for example, made of platinum, are shown as penetrating into the anode and cathode bodies; they may be simply glued to these bodies.

The anode body and the cathode body are preferably formed by compression of a powdery conductive material such as graphite mixed with the appropriate enzyme and redox mediator. A powder of a conductive polymer such as polyaniline, polypropylene, or polyvinylidene fluoride may also be used.

As an example, an anode has been prepared by mixing 350 mg of graphite particles, 110 mg of UQ, 0.5 ml of water, and glycerol (50 µl) in a ceramic mortar. Then, 7 mg of GOX and 3 mg of catalase solubilized in 100 µl of water have been incorporated to 400 mg of the previous mixture and hand mixed. A cathode has been prepared in similar fashion: 350 mg of graphite particles, 170 mg of hydroquinone, 0.3 ml of water, and 25 µl of glycerol have been mixed in a ceramic mortar. Then, 4.5 mg of PPO solubilized in 100 µl of water have been incorporated to 400 mg of the previous mixture and hand mixed. The resulting graphite-enzyme-redox mediator pastes have been compressed at a 10,000-kg/cm2 pressure to form disks. The surface and the thickness of the disks were respectively 1.33 cm2 and 0.1 cm. A platinum wire has been bonded with a conductive glue to the carbon on one side of each disk and covered with a silicon film to enhance the mechanical strength of the biocoating and the electric contact.

To operate as a cell, the anode and cathode bodies are placed in a fluid containing oxygen and a sugar, for example, glucose. The anode and cathode bodies may for example be implanted inside an animal or human body, since many locations in the body contain fluids containing glucose and oxygen.

Figure 2:
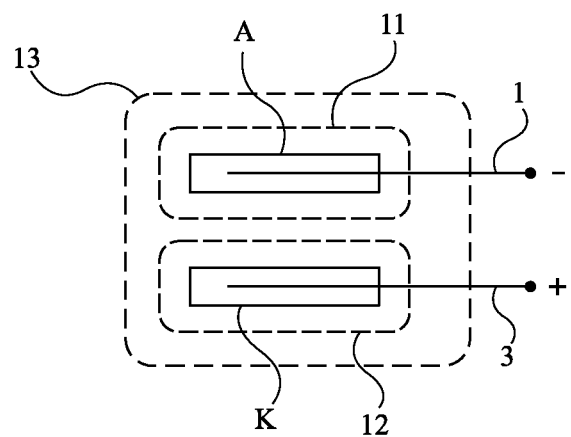
FIG. 2 very schematically shows a biofuel cell according to an embodiment of the present invention.

However, it has been observed that biofuel cells using such anode and cathode bodies have a short lifetime. The present inventors have imputed this problem to the fact that some of the redox material and/or of the enzyme leaks along time from the anode body and from the cathode body. To solve this problem, as illustrated in FIG. 2, each of the anode and cathode bodies is surrounded with a microperforated membrane, respectively 11, 12, such as membranes currently used in dialysis, which let through glucose and oxygen and prevent the passing through of the enzyme and of the redox mediator of greater molecular weight. The anode and cathode electrode assembly may be surrounded by a semipermeable membrane 13 letting through glucose and oxygen and blocking enzymes and redox mediators, especially to avoid for the anode and cathode membranes to clog, especially in case of an implantation in an animal or human body.

Glucose biofuel cells of the above type have been implanted in left lateral position in the retroperitoneal cavities of two rats respectively weighting 514 and 512 g. After stabilization of the potential in open circuit, cycles of charge and discharge have been carried out for a 12-hour period. Discharge currents from 10 to 50 microamperes have been observed.

Various embodiments with different variations have been described hereabove. It should be noted that those skilled in the art may combine various elements of these various embodiments and variations without showing any inventive step.

Such alterations, modifications and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

The invention claimed is:

1. A biofuel cell configured for use in vivo in a liquid medium containing a sugar and oxygen, wherein an anode comprises an anode enzyme capable of catalyzing the oxidation of the sugar and an anode redox mediator of low redox potential capable of exchanging electrons with the anode enzyme, and a cathode comprises a cathode enzyme capable of catalyzing the reduction of oxygen and a cathode redox mediator of high redox potential capable of exchanging electrons with the cathode enzyme, wherein
   each of the anode and cathode electrodes is formed of a solid agglomerate of a conductive material mixed with the corresponding enzyme and redox mediator and is solid with an electrode wire;
   the anode and cathode electrodes are surrounded with respective first and second semipermeable membrane letting through oxygen and glucose and blocking the enzyme and the redox mediator; and
   an assembly of the anode and cathode electrodes, including their corresponding first and second semipermeable membranes, is surrounded with a third semipermeable membrane letting through glucose and oxygen and blocking enzymes and redox mediators.

2. The biofuel cell of claim 1, wherein said first, second and third membranes are dialysis membranes.

3. The biofuel cell of claim 1, wherein the cathode mediator is selected from the group comprising quinone, 2,2'-azinobis-(3-ethylbenzo-thiazolin-6-sulphonate (ABTS), osmocene, ruthenocene, cobalt (II) tetraphenylporphyrin, and zinc phthalocyanine.

4. The biofuel cell of claim 1, wherein the cathode enzyme is selected from the group comprising polyphenol oxidase (PPO), laccase, and bilirubin oxidase.

5. The biofuel cell of claim 1, wherein the anode mediator is selected from the group comprising ubiquinone, ferrocene, cobaltocene, N-methylphenothiazine, and 8-hydroxyquinoline-5-sulfonic acid hydrate (HQS).

6. The biofuel cell of claim 1, wherein the anode enzyme is selected from the group comprising glucose oxidase, lactose oxidase, galactose oxidase, and fructose oxidase, according to the sugar to be converted.

7. The biofuel cell of claim 1, wherein the conductive material is graphite.

8. The biofuel cell of claim 1, wherein the conductive material is a conductive polymer.

* * * * *